US008779009B2

(12) United States Patent
Williams et al.

(10) Patent No.: US 8,779,009 B2
(45) Date of Patent: Jul. 15, 2014

(54) FIBER CONTAINING COMPOSITIONS AND METHODS OF MAKING AND USING SAME

(75) Inventors: Kristin Rhedrick Williams, West Chester, OH (US); Hing C. Tse, Fairfield, OH (US); Daren K. Anness, Loveland, OH (US); Harry Overly, Mooresville, NC (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/983,084

(22) Filed: Nov. 7, 2007
(Under 37 CFR 1.47)

(65) Prior Publication Data
US 2009/0123597 A1    May 14, 2009

Related U.S. Application Data

(63) Continuation-in-part of application No. 11/593,694, filed on Nov. 7, 2006, now abandoned.

(51) Int. Cl.
| *A61K 47/00* | (2006.01) |
| *A23L 1/30* | (2006.01) |
| *A23G 4/10* | (2006.01) |
| *A23G 3/42* | (2006.01) |
| *A23L 1/0534* | (2006.01) |
| *A23L 1/0522* | (2006.01) |
| *A23L 1/308* | (2006.01) |
| *A23L 1/00* | (2006.01) |
| *A23L 1/0528* | (2006.01) |

(52) U.S. Cl.
CPC . *A23L 1/308* (2013.01); *A23L 1/30* (2013.01); *A23G 4/10* (2013.01); *A23G 3/42* (2013.01); *A23L 1/0534* (2013.01); *A23L 1/0522* (2013.01); *A23L 1/0076* (2013.01); *A23V 2002/00* (2013.01); *A23L 1/0528* (2013.01); *A23V 2250/5116* (2013.01)
USPC ............................ 514/777; 514/783; 426/648

(58) Field of Classification Search
None
See application file for complete search history.

(56) References Cited

U.S. PATENT DOCUMENTS

| 4,565,702 | A |   | 1/1986 | Morley et al. |
| 4,698,232 | A |   | 10/1987 | Sheu et al. |
| 4,714,620 | A | * | 12/1987 | Bunick et al. ................. 426/572 |
| 4,724,136 | A |   | 2/1988 | Scheibl |
| 4,767,614 | A |   | 8/1988 | Scarpa et al. |
| 4,882,160 | A |   | 11/1989 | Yang et al. |
| 5,266,334 | A |   | 11/1993 | Phadke et al. |
| 5,296,209 | A |   | 3/1994 | Simone et al. |
| 5,476,678 | A |   | 12/1995 | Walter et al. |
| 5,660,872 | A |   | 8/1997 | Van Loo et al. |
| 5,858,344 | A |   | 1/1999 | Muller et al. |
| 6,080,401 | A | * | 6/2000 | Reddy et al. .................. 424/93.3 |
| 6,224,904 | B1 |   | 5/2001 | Rapp et al. |
| 6,280,769 | B1 |   | 8/2001 | D'Amelia et al. |
| 6,350,469 | B1 |   | 2/2002 | Daggy et al. |
| 6,372,253 | B1 |   | 4/2002 | Daggy et al. |
| 6,391,375 | B1 |   | 5/2002 | Fone |
| 6,399,142 | B1 |   | 6/2002 | Silver |
| 6,419,978 | B1 |   | 7/2002 | Silver |
| 6,455,068 | B1 |   | 9/2002 | Licari |
| 6,482,465 | B1 |   | 11/2002 | Cherukuri et al. |
| 6,511,679 | B2 |   | 1/2003 | D'Amelia et al. |
| 6,517,886 | B1 |   | 2/2003 | Chau et al. |
| 6,569,488 | B2 |   | 5/2003 | Silver |
| 6,673,380 | B2 |   | 1/2004 | Yang et al. |
| 6,740,350 | B2 |   | 5/2004 | Pfeiffer |
| 6,841,178 | B2 |   | 1/2005 | Cupp et al. |
| 6,904,870 | B2 |   | 6/2005 | Russell-Maynard et al. |
| 6,982,093 | B2 |   | 1/2006 | Licari |
| 7,125,562 | B2 |   | 10/2006 | Daggy et al. |
| 7,318,920 | B2 |   | 1/2008 | Christensen |
| 7,387,803 | B2 |   | 6/2008 | Licari |
| 7,452,553 | B2 |   | 11/2008 | Licari |
| 7,521,072 | B2 |   | 4/2009 | Licari |
| 2001/0012534 | A1 |   | 8/2001 | Biyani et al. |
| 2003/0026826 | A1 | * | 2/2003 | Cherukuri et al. ............. 424/440 |
| 2003/0130229 | A1 |   | 7/2003 | Del Buono et al. |
| 2003/0170371 | A1 |   | 9/2003 | Jobe et al. |
| 2003/0207003 | A1 | * | 11/2003 | Silver ............................ 426/271 |
| 2004/0141927 | A1 |   | 7/2004 | Johnson et al. |
| 2004/0191393 | A1 |   | 9/2004 | Sudha et al. |
| 2005/0089560 | A1 |   | 4/2005 | Daggy et al. |
| 2005/0089561 | A1 |   | 4/2005 | Daggy et al. |
| 2005/0089562 | A1 |   | 4/2005 | Daggy et al. |

(Continued)

FOREIGN PATENT DOCUMENTS

| EP | 0 306 469 A |   | 3/1989 |
| EP | 0 387 933 A |   | 9/1990 |
| KR | 2004093866 A | * | 11/2004 |
| RU | 2192873 |   | 11/2002 |
| WO | WO 03/105882 |   | 12/2003 |
| WO | WO 2004/022074 |   | 3/2004 |
| WO | WO 2005/056023 A1 |   | 6/2005 |
| WO | WO 2005/079603 |   | 9/2005 |
| WO | WO 2007/101115 A |   | 9/2007 |

OTHER PUBLICATIONS

Izzo, M.T., "Inulin and oligofructose in functional confections," Manufacturing Confectioner, 2002, 82 (8) 79-90, 57 ref.
Anonymous, "New functional ingredients for confectionery and chewing gum," Confectionery Production, 2000, 66 (6/7) 14-15.
De Soete, J., "Prebiotic ingredients in chewing gum. The use of inulin and oligofructose," Manufacturing Confectioner, 2000, 80 (1) 67-69.

*Primary Examiner* — Qiuwen Mi
(74) *Attorney, Agent, or Firm* — Alexandra S. Anoff

(57) ABSTRACT

A composition comprising at least about 25% of a fiber component, by weight of the composition, provides a safe and effective amount of fiber component to a user. A method of producing such a composition is provided. Additionally a method of providing a safe and effective amount of fiber component to a user is provided.

10 Claims, No Drawings

(56) References Cited

U.S. PATENT DOCUMENTS

| | | |
|---|---|---|
| 2005/0089563 A1 | 4/2005 | Daggy et al. |
| 2005/0089564 A1 | 4/2005 | Daggy et al. |
| 2005/0089565 A1 | 4/2005 | Daggy et al. |
| 2005/0118326 A1* | 6/2005 | Anfinsen et al. ............ 426/658 |
| 2005/0129823 A1 | 6/2005 | Dohl et al. |
| 2005/0142194 A1 | 6/2005 | Nocelli et al. |
| 2005/0186252 A1 | 8/2005 | Ahlgren et al. |
| 2005/0214349 A1 | 9/2005 | Nie et al. |
| 2005/0232989 A1 | 10/2005 | Piene et al. |
| 2006/0039973 A1 | 2/2006 | Aldritt et al. |
| 2006/0067922 A1* | 3/2006 | Christensen ............ 424/93.45 |
| 2006/0110476 A1 | 5/2006 | Haber et al. |
| 2006/0134183 A1 | 6/2006 | Huetter et al. |
| 2006/0216393 A1 | 9/2006 | Froseth et al. |
| 2007/0009647 A1 | 1/2007 | Huetter et al. |
| 2008/0187647 A1 | 8/2008 | Overly, III et al. |

\* cited by examiner

FIBER CONTAINING COMPOSITIONS AND METHODS OF MAKING AND USING SAME

CROSS REFERENCE TO RELATED APPLICATIONS

This application is a Continuation-In-Part of application Ser. No. 11/593,694, filed Nov. 7, 2006, and claims priority thereto under 35 USC §120.

FIELD OF THE INVENTION

The present invention relates generally to ingestible compositions, particularly to compositions that deliver fiber to a mammal, and to methods of making and using such compositions.

BACKGROUND OF THE INVENTION

It is well-known that fiber is an important part of the diet of mammals, particularly humans. Medical and nutrition professionals generally agree that dietary fiber is essential for good human health. Too little fiber in the diet is associated with diseases such as heart disease, diabetes, obesity, and colon cancer. In addition, too little fiber often results in intestinal irregularity. Proper amounts of fiber in the diet stimulate bowel movement, slow down the gastrointestinal transition and digestion processes, modify fat absorption, and increase excretion of bile acids. In addition, some dietary fibers are known to lower blood cholesterol and benefit the postprandial (after eating) glycemic response. In addition, various types of fiber and/or fiber components, for example, moderately fermentable fiber that is fermented by the intestinal flora of a user, has been shown to promote the growth and/or development of lactic acid bacteria in the gastrointestinal tract of a user, at the expense of pathogenic bacteria, thus providing benefit to the user's gastrointestinal tract.

However, it has also been documented that the average person in the United States does not eat enough dietary fiber, and often eats only about half of the recommended amount of fiber daily. Fiber intake can be increased by eating greater amounts of foods high in fiber such as grains, fruits, and vegetables. However, most consumers would have to almost double their intake of such foods to attain the recommended daily amount of fiber. Many consumers are unwilling or unable to eat large amounts of high fiber foods, and thus often look for supplements to provide the additional needed fiber.

To date there are several types and brands of fiber supplements available including powders, tablets, capsules, biscuits, breakfast cereals, laxative beverages, and the like. However, many of these compositions have certain drawbacks and are not easily accepted by consumers due to various factors such as the lack of portability, for example of powders or beverages; the unpleasant taste, and texture and/or mouthfeel of many fiber containing materials; high calories of the supplement resulting from materials used to mask the taste and/or texture of the fiber; and excess gas produced in the user by many of the fiber containing materials. In addition, flavoring, taste masking, and texture enhancing materials added to the fiber supplement products result in a lessened amount of fiber that can be included in each unit of product. Therefore, consumers must ingest increased amounts of product to obtain the desired amounts of fiber. Such unpleasant and/or inconvenient properties often result in the user discontinuing use of the product.

Recently there have been attempts to formulate fiber into a palatable, easily ingestible confectionary-type article, such as a soft chew. However, such chews are generally difficult to manufacture due to the propensity of the presence of too much fiber to result in a confection that is too hard and/or brittle for general consumer acceptance. Thus, many of the currently available confection-type products suffer from many of the noted drawbacks such as unpleasant taste and mouthfeel, high calories, and many also contain relatively small amounts of fiber, therefore requiring that the user ingest several units of product per day in order to obtain the desired amount of fiber.

Therefore, there remains a need for a palatable, low calorie, consumer acceptable, composition that can provide high amounts of fiber, as well as methods of making and using such a composition.

SUMMARY OF THE INVENTION

An embodiment of the present invention is a composition comprising at least about 25%, by weight of the composition, of a fiber component, and a humectant component, to provide a safe and effective amount of fiber to a user.

Another embodiment of the invention is an ingestible composition comprising at least about 25%, by weight of the composition, of a fiber component; a humectant component; and a surfactant component.

A further embodiment of the invention is a composition comprising at least about 25%, by weight of the composition, of a fiber component and a surfactant component.

Another embodiment of the invention is a method of delivering a safe and effective amount of fiber to a user comprising a user ingesting from about 1 unit dose to about 10 unit doses per day of a composition comprising at least about 25% of a fiber component, by weight of the composition, and a humectant component.

Additionally, an embodiment of the invention is a method of preparing a fiber containing composition comprising the steps of:
   a. adding water to a mixing vessel;
   b. adding a fiber component to the water in the mixing vessel;
   c. mixing until the fiber component is dissolved;
   d. adding a humectant component to the mixing vessel;
   e. mixing until said humectant component is dissolved; thereby creating the fiber containing composition.

Another embodiment of the invention is a method of preparing a fiber containing composition comprising the steps of:
   a. adding water to a mixing vessel;
   b. adding a fiber component to the water in the mixing vessel;
   c. mixing the water and the fiber to form a water-fiber mixture;
   d. adding a carbohydrate component to a second mixing vessel;
   e. mixing while heating the second mixing vessel to a temperature of from about 54° C. to about 77° C. to form a carbohydrate mixture;
   f. adding the water-fiber mixture to the second mixing vessel and mixing to form a carbohydrate-fiber mixture;
   g. cooking the carbohydrate-fiber mixture until solids in the carbohydrate-fiber mixture comprise from about 75% to about 85% by weight of the carbohydrate-fiber mixture, resulting in a cooked carbohydrate-fiber mixture;
   h. adding, in a jacketed mixing vessel heated to a temperature of about 57° C., a fat component and melting the fat component;

i. while melting the fat component, adding a surfactant component to the jacketed mixing vessel, to form a fat mixture;
j. mixing the fat mixture until homogeneous;
k. in a final mixing vessel, adding the fat mixture, a humectant component; an additional portion of a fiber material; and the cooked carbohydrate-fiber mixture; thereby creating a final mixture; and
l. mixing the final mixture until homogeneous.

DETAILED DESCRIPTION OF THE INVENTION

All percentages and ratios are calculated by weight unless otherwise indicated. All percentages and ratios are calculated based on the total final composition unless otherwise indicated.

Referenced herein may be trade names for components including various ingredients utilized in the present invention. The inventors herein do not intend to be limited by materials under a given trade name. Equivalent materials (e.g., those obtained from a different source under a different name or reference number) to those referenced by trade name may be substituted and utilized in the descriptions herein.

As used herein "fiber" generally means material derived from plant cell walls and which is not digestable by human digestive enzymes, including soluble fiber and insoluble fiber. The fiber component can be naturally derived or synthetic. A portion of the fiber component can be non-starch polysaccharides, including soluble and insoluble fiber.

As used herein "soluble fiber" means plant gums and oligosaccharides, or modified gums, modified celluloses, non-starch polysaccharides that are soluble in water, some of which can form viscous gels.

As used herein "humectant" means a substance having an affinity for water and which provides stabilizing action on the water content of a material. Humectants prevent loss of moisture from foods, particularly flour-containing confectioneries, prevent sugar from crystallizing, and prevent growth of ice crystals in frozen foods.

As used herein "surfactant" means a surface active agent that is both hydrophobic and hydrophilic, and is used to modify the surface properties of liquids. A surfactant is any compound that reduces surface tension when dissolved in water or water solutions, or that reduces interfacial tension between two liquids (such as water compositions and oil compositions), or between a liquid and a solid.

As used herein "carbohydrate" means sugars and digestable starches including monosaccharides, disaccharides, and polysaccharides.

As used herein in the Examples, "DE" means "dextrose equivalent", which refers to the percent of reducing sugars on a dry basis calculated as dextrose. One of skill in the art would be familiar with the measure and terminology "DE" and "dextrose equivalent". Glucose (or corn) syrups are formed by reacting a starch with an acid and/or an enzyme. DE is a measurement of the degree of hydrolysis that starches undergo. Standard corn syrups generally have a DE of about 42. The higher the DE, the sweeter the component. However, higher DE also can contribute to a composition's greater tendency to crystallize, tendency to discolor, and tendency to be more hygroscopic, and can result in lower viscosity.

Compositions

An embodiment of the present invention comprises a composition comprising at least about 25% of a fiber component, by weight of the composition, and a humectant component. The composition comprises at least about 0.001% of the humectant component, by weight of the composition.

Fiber Component

The compositions of the present invention comprises at least about 25%, alternatively at least about 30%, alternatively at least about 35%, alternatively at least about 40%, alternatively at least about 45%, alternatively at least about 50%, alternatively at least about 60%, and alternatively at least about 75%, of a fiber component, by weight of the composition.

Non-limiting examples of fiber components of the present invention can include naturally derived soluble fiber; naturally derived inulin; inulin extract; synthetic inulin; hydrolysis products of inulin commonly known as fructooligosaccharides, galacto-oligosaccharides, xylooligosaccharides, or oligo derivatives of starch; husks; brans; psyllium; polysaccharides; oligosaccharides; celluloses and derivatives thereof; starches, modified starches, and derivatives of starches; polycarbophil; lignin; arabinogalactans; chitosans; oat fiber; soluble corn fiber; non-digestible corn or wheat dextrin; locust bean gum and derivatives thereof; hydroxypropylmethyl cellulose (HPMC); pectin; and mixtures thereof.

As used herein, the term "derivative" means chemically modified, chemically or enzymatically synthesized, extracted, mechanically modified; and combinations thereof. In a preferable embodiment of the invention, the fiber component is de-sugared inulin.

In a particular embodiment of the invention, the fiber component is de-sugared inulin. Inulin is a linear oligomer comprising β-D-fructose linked to a terminal α-D-glucose. Inulin has the structural formula $GFr_n$, wherein G is α-D-glucose, Fr is β-D-fructose; and n is an integer of between 2 to 60. Inulin is often referred to as a "fructan", an "oligofructan", and an "oligofructose".

As used herein "naturally derived" means not chemically processed from its natural source. For example, inulin can be naturally derived by boiling chicory root in water then drying the resulting water portion to yield inulin.

As used herein, "de-sugared inulin" means a non-gelling form of inulin having a total of about 2% (by weight) maximum mono and disaccharides, and having about 95% (by weight) minimum soluble fiber. De-sugared inulin can be prepared by passing the water component, after boiling of chicory root in water, through a filter before drying. The filter removes mono and disaccharides.

Humectant Component

An embodiment of the composition of the present invention can comprise a humectant component, which comprises at least about 0.001%, alternatively from about 0.001% to about 20%, alternatively from about 0.001% to about 10%, and alternatively from about 0.001% to about 5%, by weight of the composition.

Non-limiting examples of suitable humectant components include glycerin, invert sugar, polyhydric alcohols, sorbitol, polyethylene glycol, propylene glycol, polyglycerol, gelatin, xanthan gums, carageenans, alginates, cyclomethicone, sodium hyaluronate, sodium lactate, tracetin, triethanolamine, and mixtures thereof.

The humectant component can also be a mixture of humectants such as for example, the humectant component can be a mixture of glycerin and sorbitol present in the humectant component in a weight ratio of from about 2:1 to about 12:1, alternatively from about 2:1 to about 10:1, and alternatively from about 3:1 to about 5:1.

Surfactant Component

Embodiments of the compositions of the present invention can include at least about 0.01%, by weight of the composition, of a surfactant component. Alternatively the surfactant component can comprise from about 0.01% to about 20%, alternatively from about 0.01% to about 10%, alternatively from about 0.01% to about 5%, and alternatively from about 0.01% to about 3%, by weight of the composition.

Non-limiting examples of suitable surfactant components include polyglycerol esters, glycerophospholipids, mono- and di-glycerides, sucrose monoesters, sorbitan esters, polyethoxylated glycols, agar, albumin, casein, glyceryl monostearate, gums, soaps, irish moss, egg yolk, lecithin, and mixtures thereof. For example, the surfactant component can be lecithin.

Carbohydrate Component

Embodiments of the compositions of the present invention can also include at least about 1%, alternatively less than about 50%, alternatively from about 5% to about 50%, alternatively from about 5% to about 45%, and alternatively from about 5% to about 40%, by weight of the composition, of a carbohydrate component.

Non-limiting examples of suitable carbohydrate components include reducing sugars, non-reducing sugars, corn syrup, sucrose, liquid sucrose, polydextrose, trehalose, fructose, lactose, maltose, honey, glucose, galactose, and mixtures thereof. Non-limiting examples of reducing sugars include corn syrups, fructose, and milk sugars (i.e. lactose). A non-limiting example of a non-reducing sugar is sucrose.

For example, the carbohydrate component can be a mixture of a non-reducing sugar such as sucrose and a reducing sugar such as corn syrup present in the carbohydrate component in a weight ratio of from about 1:1.1 to about 7:1, alternatively from about 1:1.1 to about 1:5, and alternatively from about 1:1.1 to about 1:3.

Fat Component

Optionally, embodiments of the compositions of the present invention can also include a lipid or fat component comprising less than about 20%, alternatively less than about 15%, and alternatively less than about 10%, by weight, of the composition.

Non-limiting examples of suitable fat components of the present invention include plant oils; hydrogenated plant oils; partially hydrogenated plant oils such as soybean oil and partially hydrogenated coconut oil; animal fats; fat substitutes such as olestra; fatty acids, and mixtures thereof.

Probiotic Components

Embodiments of the compositions of the present invention can also include a "probiotic" component. As used herein, "probiotic" means a microorganism that is beneficial to the host organism, versus pathogenic microorganisms that are detrimental to the host organism. Non-limiting examples of probiotic components include various strains of bacteria including *Lactobacillus* and *Bifidobacterium* species of bacteria, such as *Lactobacillus acidophilus, Bifidobacterium infantis, Bifidobacterium bifidum* and the like, and mixtures thereof.

The compositions of the present invention can include at least about 0.001%, by weight of the composition, of a probiotic component. Alternatively, the compositions of the present invention can include from about 0.001% to about 10%, alternatively from about 0.01% to about 5%, and alternatively from about 0.1% to about 5%, by weight of the composition, of a probiotic component.

Supplement Components

Additionally, embodiments of the compositions of the present invention can include supplements such as, but not limited to, vitamins, minerals, herbs, botanicals, plant derived supplements, animal derived supplements, therapeutic compounds, and mixtures thereof.

Non-limiting examples of such other components include: calcium, potassium, B vitamins, vitamins A, C, D, E, and K, folic acid, other vitamins and minerals commonly known in the art and used for supplementing the diet; extracts and active phytochemicals including ferulic acid (from apples), ginseng, ginko biloba, beta carotene, capsicanoids, anthocyanidins, bioflavinoids, d-limonene, isothiocyanates, cysteines from garlic, ginger, grapes, catechins and polyphenols from teas, onions, phytosterols, isoflavones, lycopene, curcumin, caffeine; glucosamine, chondroitin, msm; melatonin, seratonin; and mixtures thereof.

The compositions of the present invention can include at least about 0.001%, by weight of the composition, of a supplement component. Alternatively, the composition of the present invention can include from about 0.001% to about 25%, alternatively from about 0.01% to about 10%, and alternatively from about 0.1% to about 5%, by weight of the composition, of a supplement component.

Flavor, Sweetener, Colorant and Preservative Components

Various additional components including natural and artificial flavors, natural and artificial sweeteners, and natural and artificial colorants and/or food grade dyes can be included in the compositions of the present invention. In addition, various preservatives, as would be understood by those of ordinary skill in the art can also be added.

Non-limiting examples of flavors include natural or artificial flavors and include chocolate; vanilla; caramel; coffee; fruit flavors including lemon, lime, orange, blackberry, raspberry, blueberry, peach, apricot, cherry, grape; and mixtures thereof. Such flavors can be purchased, and/or prepared and added using known flavor technologies.

Non-limiting examples of natural sweeteners include sugars and starches such as sucrose, glucose, fructose, lactose, maltose, corn starch, and mixtures thereof. Non-limiting examples of artificial sweeteners include sucralose, acesulfame potassium, aspartame, saccharin, lactitol, stevia, Neohesperidine DC, polydextrose, cyclamates, sugar alcohols, isomalt, and mixtures thereof.

Non-limiting examples of suitable preservatives include: sodium benzoate, sodium citrate, sodium phosphate, potassium metabisulfite, sodium metabisulfite, sodium lactate, sodium sulfite, EDTA (ethylenediaminetetraacetic acid), methylparaben, and mixtures thereof.

The compositions of the present invention can include at least about 0.001%, by weight of the composition, of flavor, sweetener, colorant and/or preservative components, and mixtures thereof. Alternatively, the compositions of the present invention can include from about 0.001% to about 10%, alternatively from about 0.001% to about 5%, and alternatively from about 0.001% to about 2%, by weight of the composition, of flavor, sweetener, colorant components and/or mixtures thereof.

Form of Composition

The compositions of the present invention can be formed into any suitable, ingestible form. Non-limiting examples of the form of the compositions include: soft chew, hard chew, chewable tablet, nutritional bar, lozenge, powder, granules, clusters, soft gel, semi-solid taffy-like chew, chewing gum, swallowable tablet, swallowable capsule, swallowable caplet, individual unit doses, user-dosable forms, and mixtures thereof. For example, a unit dose can be a single soft chew, or a partitionable form such as a bar which the user cuts or breaks to provide unit dosages.

Methods of Making

Example methods of preparing compositions of the present invention can comprise steps selected from the steps of:

Adding water to a mixing vessel, at a temperature of about 25° C.; and

Mixing, at high or low shear, and adding a fiber component to the water in the mixing vessel until the fiber component is dissolved, and no visible lumps remain, to form a fiber-water mixture. This step can be done at about 25° C., or can be done heated at temperatures of from about 55° C. to about 60° C.

The resultant fiber-water mixture is highly viscous.

A humectant component can be added while mixing the fiber and water by adding a humectant component to the mixing vessel and mixing until the mixture is homogeneous, thereby forming a fiber-humectant mixture. Additional fiber component can optionally be added to the fiber-humectant mixture at this step. Flavor, sweetener, color, and/or preservative components can be added at this step also.

Such a mixture can then be processed in a mold, via a mold process, or extruded, as would be understood by one of ordinary skill in the art, and formed into unit dose forms such as soft chews that can be packaged individually into poly-lined foil wrappers (such as Inner Wraps 32700X available from Flexible Packaging, Toronto, Ontario, Canada). The foil wrapped chews can then be placed in secondary packaging, non-limiting examples of which include glass bottles; plastic bottles; foil lined bags, cartons, or sleeves; and combinations thereof.

Embodiments of the invention can include additional steps, after mixing a fiber component and water, and before preparing the final composition, such as adding a carbohydrate component, and/or a fat component, and/or flavor, sweetener, color, and preservative component. Such components can be prepared as separate "premixes" generally as follows.

Carbohydrate Component Premix

For preparation of a carbohydrate component, steps include:

Combining a non-reducing sugar and a reducing sugar in a mixing vessel to form a carbohydrate mixture; and Heating the carbohydrate mixture to a temperature of between about 130° F. to about 170° F. (about 54° C. to about 77° C.), alternatively to a temperature of about 165° F. (about 74° C.).

Once the carbohydrate mixture is formed it can be combined with the fiber-water mixture, or fiber-humectant mixture, by: adding to the carbohydrate mixture the fiber-water mixture and heating at a temperature of about 165° F. (about 74° C.) for about 15 minutes, until a homogeneous carbohydrate-fiber slurry is produced. The carbohydrate-fiber mixture is cooked until the solids content is between about 75% and 85%, alternatively between about 80% and 82%, by weight of the resulting cooked carbohydrate-fiber mixture. The cooked carbohydrate-fiber mixture can then be combined with a fat mixture as described below. The carbohydrate-fiber mixture can be stored temporarily in a jacketed holding vessel until needed. As would be understood by one of skill in the art, a jacketed vessel can be easily heated or cooled.

Fat Premix

For preparation of a fat component, steps include:

Heating a jacketed vessel to a temperature of from about 125° F. (about 52° C.) to about 170° F. (about 77° C.), alternatively from about 145° F. (about 63° C.) to about 165° F. (about 74° C.); alternatively to about 150° F. (about 66° C.).

Adding a fat component to the jacketed vessel and melting the fat component while stirring;

While stirring, adding a surfactant component and optionally flavor components such as milk compounds and/or cocoa;

Mixing until the mixture is homogeneous, about 15 minutes.

The fat mixture can be stored temporarily in a jacketed holding vessel until needed.

To create the final mixture, the fat mixture can be combined with the cooked carbohydrate-fiber component as described below.

Final Mixture

For preparation of the final mixture, steps can include:

Adding, in a separate mixing vessel, at about 25° C., the fat mixture and mixing the fat mixture;

Optionally adding a humectant component if not already added into the fiber-water mixture and mixing;

Adding a portion of dry fiber component and mixing;

Optionally adding sweetener, color, and/or preservative components and mixing;

Adding the cooked carbohydrate-fiber mixture, via pipes connected from the vessel containing the cooked carbohydrate-fiber mixture to the vessel containing the final mixture, the pipes being heated to a temperature of about 180° F. (about 82° C.) to maintain the cooked carbohydrate-fiber mixture at a temperature of between about 130° F. to about 170° F. (about 54° C. to about 77° C.), and mixing;

Optionally adding flavor components and mixing; and

Unloading the final mixture into one or more transfer totes (vessels used to transfer the final mixture from the mixing vessel into a pre-kneader); and Processing the final mixture via extrusion through either a single or double screw extruder, alternatively a double screw extruder, to produce an extrudate that can be formed into individual unit soft chew dosages.

It may be advantageous to coat the interior of the transfer tote with a food grade transfer aid, non-limiting examples of which include soybean oil and corn starch.

Extrusion can be done, for example by adding the final mixture, adjusted to a temperature of from about 100° F. (about 38° C.) to about 120° F. (about 49° C.), to a pre-kneader, then into a final rope extruder; cooling via a cooling tunnel (cooled to from about 40° F. (about 5° C.) to about 80° F. (about 27° C.)), and knife cutting into individual pieces to form soft chews.

The temperature of the final mixture, before delivery into the pre-kneader can be adjusted in various ways, non-limiting examples of which include: making the final mixture in a jacketed vessel, adjusting the temperature of either or both the cooked carbohydrate-fiber mixture and/or the fat mixture in the holding vessel(s) prior to adding to the final mixing vessel, and combinations thereof.

The soft chews can be wrapped in poly-lined foil wrappers (such as Inner Wraps' 32700X available from Flexible Packaging, Toronto, Ontario, Canada) or other protective barriers. The foil wrapped chews can then be placed in secondary packaging, non-limiting examples of which include glass bottles; plastic bottles; foil lined bags, cartons, or sleeves; and combinations thereof.

Methods of Using

Embodiments of the present invention also includes methods of delivering a safe and effective amount of a fiber component to a user. As used herein, a "safe and effective amount" means an amount of fiber component effective to deliver one or more of the following benefits: Taxation; increased stool volume and moisture content; intestinal regularity; slowed gastrointestinal transition and digestion processes; modified fat absorption; aiding in weight management; increasing excretion of bile acids; aiding in lowering blood cholesterol; benefiting the postprandial glycemic response; aiding growth and/or development of beneficial gastrointestinal microorganisms; as well as helping to reduce the risk of heart disease, diabetes, obesity, and colon cancer.

A method of delivering a safe and effective amount of fiber component to a user comprises the user ingesting from about 1 to about 20 unit doses per day of a composition comprising at least about 25% of a fiber component, by weight of the composition; and a humectant component.

To deliver a desired amount of fiber component per day, a user can ingest from about 1 to about 20, alternatively from about 1 to about 10, and alternatively from about 1 to about 5 unit doses of the composition per day, i.e. for example, from about 1 to about 20 soft chews per day. Each unit dose can comprise from about 1 to about 3 grams of fiber component, and alternatively from about 2 to about 2.5 grams of fiber component. Therefore, for example, if a user wished to ingest 10 grams of fiber per day, the user would ingest from about 4 to about 5 unit doses per day. If the user wished to ingest 20 grams of fiber per day, the user would ingest about 10 unit doses per day.

EXAMPLES

The following examples are included for illustrative purposes only and are not intended to in any way limit the scope of the present invention.

Tables I and II show various example compositions of the present invention. Examples of compositions that can be made by the processes of Examples 1-5 are shown in Table I.

Example 1

Fiber Component Plus Humectant Component
Inulin/Sorbitol Composition

At room temperature, about 25° C., add 38.89 grams of purified water to a mixing vessel and mix with a Silverson L4RT-A high shear mixer. Add 50 grams of de-sugared inulin (available as Oliggo-Fiber De-Sugared Inulin from Cargill, Minneapolis, Minn., USA) while mixing at medium speed until the inulin is dissolved and no lumps are visible. Slowly add 10 grams of a 70% sorbitol solution (available from Archer Daniels Midland Company (ADM), Decatur, Ill., USA) to the mixture and mix at constant speed until a homogeneous mixture is formed. Add 1.11 grams of flavor/sweetener/color mixture to the inulin-sorbitol mixture to achieve a desired flavor, sweetness and color. Mix the composition until no lumps or undissolved flavor or color components are visible. Add the final mixture to a hopper, pour into a mold and eject from mold once product "cures" (firms to its final state). Individual pieces can be wrapped in poly-lined foil wrappers (such as Inner Wraps 32700X available from Flexible Packaging, Toronto, Ontario, Canada) and packaged into bottles (available from Setco, Anaheim, Calif., USA) for secondary packaging.

Example 2

Fiber Component plus Humectant Component
Inulin/Glycerin Composition

At room temperature, about 25° C., add 38.89 grams of purified water to a mixing vessel and mix with a Silverson L4RT-A high shear mixer. Add 50 grams of de-sugared inulin (available as Oliggo-Fiber De-Sugared Inulin from Cargill, Minneapolis, Minn., USA) while mixing at medium speed until the inulin is dissolved and no lumps are visible. Slowly add 10 grams of glycerin (available as glycerin 99% USP Kosher from Penta Manufacturing Company, Fairfield, N.J., USA) to the mixture and mix at constant speed until the glycerin is fully mixed. Add 1.11 grams of flavor/sweetener/color mixture to the inulin glycerin mixture to achieve a desired flavor, sweetness and color. Mix the composition until no lumps or undissolved flavor or color components are visible. Add the final mixture to a hopper, pour into a mold and eject from mold once product "cures" (firms to its final state). Individual pieces can be wrapped in poly-lined foil wrappers (such as Inner Wraps 32700X available from Flexible Packaging, Toronto, Ontario, Canada) and packaged into bottles (available from Setco, Anaheim, Calif., USA) for secondary packaging.

Example 3

Fiber Component plus Two Humectants

Add 120 grams of purified water to a mixing vessel at about 25° C. and mix using a Silverson L4RT-A high shear mixer. While stirring the water, add 280 grams of crystalline sorbitol (available as crystalline sorbitol 834, NF from SPI Pharma, New Castle, Del., USA) to the mixture and mix at constant speed until the sorbitol is fully dissolved. While mixing the water-sorbitol solution add 1200 grams of glycerin (available as glycerin 99% USP Kosher from Penta Manufacturing Company, Fairfield, N.J., USA) and 2400 grams of high fructose corn syrup (available as 55% concentration from Tate & Lyle Ingredients Americas, Decatur, Ill.). While mixing the above solution, add 6000 grams of de-sugared inulin (available as Oliggo-Fiber De-Sugared Instant from Cargill) and mix until no lumps are visible. Add 200 grams of flavor/sweetener/color mixture to obtain the desired flavor, sweetness and color. Mix the composition until no lumps or un-dissolved flavor or color components are visible. Add the final mixture to a hopper, pour into a mold and eject from mold once product "cures" (firms to its final state). Individual pieces can be wrapped in poly-lined foil wrappers (such as Inner Wraps 32700X available from Flexible Packaging, Toronto, Ontario, Canada) and packaged into bottles (available from Setco, Anaheim, Calif., USA) for secondary packaging.

Example 4

Fiber Component plus Surfactant Component
Inulin/Lecithin Composition

Add 30 kilograms of purified water to a mixing vessel at about 25° C. Add 30 kilograms of de-sugared inulin (available as Oliggo-Fiber De-Sugared Instant from Cargill) to the water and mix using an Arde Barinco piston homogenizer (available from Arde Barinco, Norwood, N.J., USA) until the inulin is dissolved and no lumps are visible. Add 3 kilograms of lecithin (available as Lecithin, NF from Central Soya Company) to the mixture and mix with a piston homogenizer until the lecithin is completely mixed. Slowly add an additional 30 kilograms of de-sugared inulin to the mixture in the homogenizer and mix until no lumps are visible. Once the additional inulin is dissolved and no lumps are visible, add 5 kilograms of flavor/sweetener/color mixture to obtain the desired flavor, sweetness and color profile. Mix in the composition until no lumps or un-dissolved flavor or color components are visible.

Add the final mixture to a hopper, pour into a mold and eject from mold once product "cures" (firms to its final state). Individual pieces can be wrapped in poly-lined foil wrappers (such as Inner Wraps 32700X available from Flexible Packaging, Toronto, Ontario, Canada) and packaged into bottles (available from Setco, Anaheim, Calif., USA) for secondary packaging.

Example 5

Fiber Component plus Humectant plus Probiotic

At room temperature, about 25° C., add 140 grams of de-sugared inulin, 10 grams of crystalline sorbitol (available as crystalline sorbitol 834, NF from SPI Pharma), 20 grams of Bifantis™35624 (bifido bactierium, Chr. Hansen, Denmark), and 30 grams of microcrystalline cellulose (available as Avicel from FMC, Philadelphia, Pa., USA) to a V-blender. Tumble the mixture at 15 rpm for at least about 5 minutes, until no lumps are visible.

Add 3 grams of flavor/sweetener/color mixture to achieve a desired flavor, sweetness, and/or color. Mix the composition until no lumps or un-dissolved flavor or color are visible. Add the final mixture to a tablet hopper, compress into a tablet and eject from a tablet press. The tablets can be packaged into bottles (available from Setco, Anaheim, Calif., USA).

Examples of compositions that can be made by the processes of Examples 6-9 are shown in Table II.

Example 6

Fiber Component plus Humectant, Surfactant, Carbohydrate and Fat Components

Fiber-Water Premix

At room temperature, about 25° C., add 200 kilograms of purified water to a mixing vessel having a Eurostar low shear mixer with marine propeller blades. While stirring the water, slowly add 200 kilograms of de-sugared inulin (available as Oliggo-Fiber De-Sugared Instant from Cargill). Mix the solution for at least about 15 minutes until all inulin is dissolved in the water and no lumps are visible, thus forming a fiber-water premix.

Carbohydrate Component Premix

In a separate vessel, add 174 kilograms of liquid sucrose (available from Imperial Sugar) and 261 kilograms of corn syrup 43 DE (available from Cargill Foods; Clearsweet 43Corn Syrup) and heat to a temperature of about 165° F. (about 74° C.) to yield the carbohydrate premix. Once the carbohydrate premix is at a temperature of about 165° F. (about 74° C.), add 315 kilograms of the fiber-water premix and mix for about 15 minutes until a homogeneous carbohydrate-fiber slurry is produced. Cook the carbohydrate-fiber mixture until the solids in the composition comprise about 80.3% to about 81.0% by weight of the composition. After cooking, if approximately 80.6% solids remain, the resulting cooked carbohydrate-fiber mixture weighs about 492 kilograms. Following cooking, store the cooked carbohydrate-fiber mixture in a jacketed holding vessel and maintain at a temperature of from about 130° F. (about 54° C.) to about 170° F. (about 77° C.) until the cooked carbohydrate-fiber mixture is mixed into the final mixture.

Fat Premix

Heat a jacketed vessel to about 135° F. (about 57° C.), and add 111 kilograms of partially hydrogenated coconut oil (available as Neutresca 55-43 Kosher from AarhusKarlshamm, Malmo, Sweden) to the heated vessel and melt while stirring with a Eurostar mixer utilizing marine propeller blades. While stirring, add 5.6 kilograms of soy lecithin (available as Lecithin, NF from Central Soya Company, Ft. Wayne, Ind., USA), 34.9 kilograms of milk powder or solids (available as NFDM High Heat from Kraft, Northfield, Ill., USA), and 81.4 kilograms of cocoa powder (available as cocoa powder 22/24 NP from Callebaut, Zurich, Switzerland) to the mixer. Mix the resulting fat mixture for at least about 15 minutes, while continuing heating, until the fat mixture is homogeneous. Store the fat mixture in a jacketed holding vessel and maintain at a temperature of from about 125° F. (about 52° C.) to about 170° F. (about 77° C.) until the fat mixture is mixed into the final mixture.

Final Mixture

In a separate mixing vessel, at about 25° C., and having a Z-arm mixer, add 232.6 kilograms of fat mixture and mix for about 30 seconds with the mixer in forward mode, and about 30 seconds with the mixture in reverse mode. Next, add 57 kilograms of glycerin (available as glycerin 99% USP Kosher from Penta Manufacturing Company), 390 kilograms of dry de-sugared inulin (a second addition of inulin), 5.06 kilograms of sodium chloride, 0.18 kilograms of sucralose (available as Splenda® sucralose powder from McNeil Specialty Products, Ft. Washington, Pa., USA), and 0.04 kilograms of acesulfame postassium (available as Sunnett from Nutrinova, Dallas, Tex., USA) and mix for about 1 minute. Next, add 298.35 kilograms of cooked carbohydrate-fiber mixture, via pipes heated with steam to a temperature of about 180° F. (about 82° C.), in order to maintain the temperature of the cooked carbohydrate-fiber mixture, and mix for about 1 minute. Add 1.9 kg of chocolate flavor (available from Firmenich as N&A Chocolate Flavor #057677B), 0.64 kg of caramel flavor (available from Firmenich as Nat. Caramel #598611T), and 0.32 kg of vanilla cream flavor (available from Firmenich as Art. Cream #059200A) to the Z-arm mixer, and mix for about 4 minutes to form the final mixture. Unload the vessel containing the final mixture into 1-2 transfer totes (vessels used to transfer material from the mixing vessel to the pre-kneader) at room temperature. Add the final mixture, adjusted to a temperature of from about 100° F. (about 38° C.) to about 120° F. (about 49° C.) to a pre-kneader, then to a final rope extruder and extrude into ropes, cool the ropes via a cooling tunnel (cooled to from about 40° F. (about 5° C.) to about 80° F. (about 27° C.)), and knife cut into individual pieces to form soft chews. Individual chews can be wrapped in poly-lined foil primary wrappers (available as Inner Wraps 32700X available from Flexible Packaging, Toronto, Ontario, Canada).

Example 7

Vanilla Chew Example

Fiber Water Premix

At room temperature, about 25° C., add 140 kilograms of purified water to a vessel having a Eurostar low shear mixer with marine propeller blades. Heat the water to a temperature between about 55° C. to about 60° C. While stirring the water, add 140 kilograms of de-sugared inulin (available as Oliggo-Fiber De-Sugared Instant from Cargill). Mix the solution for at least about 15 minutes, until all inulin is dissolved in the water and no lumps are visible thus forming a fiber-water premix.

Carbohydrate Component Premix

In a separate vessel, add 124 kilograms of liquid sucrose (available from Imperial Sugar) and 154 kilograms of corn syrup 43 DE (available from Cargill Foods; Clearsweet 43Corn Syrup) and heat to about 165° F. (about 74° C.) to yield the carbohydrate premix. Once the carbohydrate premix is at about 165° F. (about 74° C.), maintain the carbohydrate premix at a temperature of between about 130° F. to about 170° F. (about 54° C.-77° C.) and add 201 kilograms of the fiber-water premix and mix for about 15 minutes until a homogeneous carbohydrate-fiber slurry is produced. Cook the carbohydrate-fiber mixture until the solids in the composition comprise from about 80.3% to about 81.0% by weight of the composition. After cooking, if approximately 80.6% solids remain, the resulting cooked carbohydrate-fiber mixture weighs about 317 kilograms. Following cooking, store the cooked carbohydrate-fiber mixture in a jacketed holding vessel and maintain at a temperature of from about 130° F. (about 54° C.) to about 170° F. (about 77° C.) until the cooked carbohydrate-fiber mixture is mixed into the final mixture.

Fat Premix

Heat a jacketed vessel to about 135° F. (about 57° C.), and add 114 kilograms of partially hydrogenated coconut oil (available as Neutresca 55-43 Kosher from AarhusKarshamm) to the heated vessel and melt while stirring with a Eurostar mixer utilizing marine propeller blades. While stirring, add 13 kilograms of soy lecithin (available as Lecithin, NF from Central Soya Company) and 91 kilograms of milk powder or solids (available as NFDM High Heat from Kraft, Northfield, Ill., USA). Mix the resulting fat mixture for at least about 15 minutes, while continuing heating, until the fat mixture is homogeneous. Store the Fat mixture in a jacketed holding vessel and maintain at a temperature of from about 125° F. (about 52° C.) to about 170° F. (about 77° C.) until the fat mixture is mixed into the final mixture.

Final Mixture

In a separate mixing vessel, at approximately 25° C., and having a Z-arm mixer, add 90.7 kilograms of fat mixture and 12.7 kilograms of glycerin (available as glycerin 99% USP Kosher from Penta Manufacturing Company), and mix for about 30 seconds with the mixer in forward mode, and about 30 seconds with the mixture in reverse mode. Next, add 98.1 kilograms of dry de-sugared inulin and mix for one minute. Add, via pipes heated to about 180° F. (about 82° F.) to maintain the temperature of the cooked carbohydrate-fiber mixture, 150.05 kilograms of cooked carbohydrate-fiber mixture, and mix for about 1 minute. Add 12.7 kilograms of glycerin, and 98.1 kilograms of dry inulin and mix for at least 1 minute or until a homogeneous mixture is formed. Add 18 kilograms of sugar (available from Imperial Sugar, Sugarland, Tex., USA), 0.08 kilograms of sucralose (available as Splenda® sucralose powder from McNeil Specialty Products), and 0.01 kilograms of acesulfame postassium (available as Sunnett from Nutrinova) and mix for about 1 minute. Next, add 150.06 kilograms of cooked carbohydrate-fiber mixture, via pipes heated with steam to a temperature of about 180° F. (about 82° C.) in order to maintain the temperature of the cooked carbohydrate-fiber mixture, and mix for about 1 minute. While the mixer is in operation, add 4.5 kilograms of vanilla flavor (available as Firmenich N&A French Vanilla 5686847) to the Z-arm mixer, and mix for about 5 minutes to form the final mixture. Unload the vessel containing the final mixture into 1-2 transfer totes (vessels used to transfer material from the mixing vessel to the pre-kneader) at room temperature. Add the final mixture, adjusted to a temperature of from about 100° F. (about 38° C.) to about 120° F. (about 49° C.) to a pre-kneader, then to a final rope extruder and extrude into ropes, cool the ropes via a cooling tunnel (cooled to from about 40° F. (about 5° C.) to about 80° F. (about 27° C.)), and knife cut into individual pieces to form soft chews. Individual chews can be wrapped in poly-lined foil primary wrappers (available as Inner Wraps 32700X available from Flexible Packaging, Toronto, Ontario, Canada).

Example 8

Chocolate Chew Example

Fiber Water Premix

At room temperature, about 25° C., add 140 kilograms of purified water to, a vessel having a Eurostar low shear mixer with marine propeller blades. Heat the water to a temperature between about 55° C. to about 60° C. While stirring the water, add 140 kilograms of de-sugared inulin (available as Oliggo-Fiber De-Sugared Instant from Cargill). Mix the solution for at least about 15 minutes, until all inulin is dissolved in the water and no lumps are visible, thus forming a fiber-water premix.

Carbohydrate Component Premix

In a separate vessel, add 124 kilograms of liquid sucrose (available from Imperial Sugar) and 154 kilograms of corn syrup 43 DE (available from Cargill Foods; Clearsweet 43Corn Syrup) and heat to a temperature of about 165° F. (about 74° C.) to yield the carbohydrate premix. Once the carbohydrate premix is at about 165° F. (about 74° C.), maintain the carbohydrate premix at between about 130° F. to about 170° F. (about 54° C.-77° C.) and add 201 kilograms of the fiber-water premix and mix for about 5 minutes until a homogeneous carbohydrate-fiber slurry is produced. Cook the carbohydrate-fiber mixture until the solids in the composition comprise from about 80.3% to about 81.0% by weight of the composition. After cooking, if approximately 80.6% solids remain, the resulting cooked carbohydrate-fiber mixture weighs about 317 kilograms. Following cooking, store the cooked carbohydrate-fiber mixture in a jacketed holding vessel and maintain at a temperature of from about 130° F. (about 54° C.) to about 170° F. (about 77° C.) until the cooked carbohydrate-fiber mixture is mixed into the final mixture.

Fat Premix

Heat a jacketed vessel to a temperature of about 135° F. (about 57° C.), and add 114 kilograms of partially hydrogenated coconut oil (available as Neutresca 55-43 Kosher from AarhusKarshamm) to the heated vessel and melt while stirring with a Eurostar mixer utilizing marine propeller blades. While stirring, add 13 kilograms of soy lecithin (available as Lecithin, NF from Central Soya Company) to the mixer. Also add 91 kilograms of milk solids (available as NFDM High Heat from Kraft). Mix the resulting fat mixture for at least about 10 minutes, while continuing heating, until the fat mixture is homogeneous. Store the fat mixture in a jacketed holding vessel and maintain at a temperature of from about 125° F. (about 52° C.) to about 170° F. (about 77° C.) until the fat mixture is mixed into the final mixture.

Final Mixture

In a separate mixing vessel, at about 25° C., and having a Z-arm mixer, add 114.7 kilograms of fat mixture and 14 kilograms of glycerin (available as glycerin 99% USP Kosher from Penta Manufacturing Company) and mix for about 30 seconds with the mixer in forward mode, and about 30 seconds with the mixture in reverse mode. Next, add 96.2 kilograms of dry de-sugared inulin, 2.5 kilograms of sodium chloride, 0.09 kilograms of sucralose (available as Splenda® sucralose powder from McNeil Specialty Products), and 0.02 kilograms of acesulfame postassium (available as Sunnett from Nutrinova) and mix for about 2 minutes. Add 147.1 kilograms of cooked carbohydrate-fiber mixture via pipes heated with steam to a temperature of about 180° F. (about 82° C.) in order to maintain the temperature of the cooked carbohydrate-fiber mixture, and mix for about 1 minute. Add 14 kilograms of glycerin, and 96.2 kilograms of dry inulin and mix for about 2 minutes. Next, add 147.1 kilograms of cooked carbohydrate-fiber mixture and mix for about 1 minute. While the mixer is running, add 2.7 kilograms of vanilla flavor and 0.3 kilograms of caramel flavors (available as Givaudan Vanilla 10824-73 and Givaudan Caramel Toffee 11889-33), and mix for about 5 minutes to form the final mixture. Unload the vessel containing the final mixture into 1-2 transfer totes (vessels used to transfer material from the mixing vessel to the pre-kneader) at room temperature. Add the final mixture, adjusted to a temperature of from about 100° F. (about 38° C.) to about 120° F. (about 49° C.) to a pre-kneader, then to a final rope extruder and extrude into ropes, cool the ropes via a cooling tunnel (cooled to from about 40° F. (about 5° C.) to about 80° F. (about 27° C.)), and knife cut into individual pieces to form soft chews. Individual chews can be wrapped in poly-lined foil primary wrappers (available as Inner Wraps 32700X available from Flexible Packaging, Toronto, Ontario, Canada).

Example 9

Chocolate Chew Example

Fiber Water Premix

At room temperature, about 25° C., add 140 kilograms of purified water to a vessel having a Eurostar low shear mixer with marine propeller blades. Heat the water to a temperature between about 55° C. to about 60° C. While stirring the water, add 140 kilograms of de-sugared inulin (available as Oliggo-Fiber De-Sugared Instant from Cargill). Mix the solution for at least about 15 minutes, until all inulin is dissolved in the water and no lumps are visible, thus forming a fiber-water premix.

Carbohydrate Component Premix

In a separate vessel, add 124 kilograms of liquid sucrose (available from Imperial Sugar) and 154 kilograms of corn syrup 43 DE (available from Cargill Foods; Clearsweet 43Corn Syrup) and heat to about 165° F. (about 74° C.) to yield the carbohydrate premix. Once the carbohydrate premix is at a temperature of about 165° F. (about 74° C.), maintain the carbohydrate premix at between about 130° F. to about 170° F. (about 54° C. to about 77° C.) and add 201 kilograms of the Fiber-Water premix and mix for about 5 minutes until a homogeneous carbohydrate-fiber slurry is produced. Cook the carbohydrate-fiber mixture until the solids in the composition comprise from about 80.3% to about 81.0% by weight of the composition. After cooking, if approximately 80.6% solids remain, the resulting cooked carbohydrate-fiber mixture weighs about 317 kilograms. Following cooking, store the cooked carbohydrate-fiber mixture in a jacketed holding vessel and maintain at a temperature of from about 130° F. (about 54° C.) to about 170° F. (about 77° C.) until the cooked carbohydrate-fiber mixture is mixed into the final mixture.

Fat Premix

Heat a jacketed vessel to a temperature of about 135° F. (about 57° C.), and add 114 kilograms of partially hydrogenated coconut oil (available as Neutresca 55-43 Kosher from AarhusKarshamm) to the heated vessel and melt while stirring with a Eurostar mixer utilizing marine propeller blades. While stirring, add 13 kilograms of soy lecithin (available as Lecithin, NF from Central Soya Company) to the mixer. Also add 91 kilograms of milk solids (available as NFDM High Heat from Kraft) to the mixer. Mix the resulting fat mixture for at least about 10 minutes, while continuing heating, until the fat mixture is homogeneous. Store the fat mixture in a jacketed holding vessel and maintain at a temperature of from about 125° F. (about 52° C.) to about 170° F. (about 77° C.) until the fat mixture is mixed into the final mixture.

Final Mixture

In a separate mixing vessel, at about 25° C., and having a Z-arm mixer, add 114.7 kilograms of fat mixture and 28 kilograms of glycerin (available as glycerin 99% USP Kosher from Penta Manufacturing Company) and mix for about 30 seconds with the mixer in forward mode, and about 30 seconds with the mixture in reverse mode. Next, add 192.4 kilograms of dry de-sugared inulin, 2.5 kilograms of sodium chloride, 0.09 kilograms of sucralose (available as Splenda® sucralose powder from McNeil Specialty Products), and 0.02 kilograms of acesulfame postassium (available as Sunnett from Nutrinova) and mix for about 2 minutes. Add 294.3 kilograms of cooked carbohydrate-fiber mixture, via pipes heated with steam to a temperature of about 180° F. (about 82° C.) in order to maintain the temperature of the cooked carbohydrate-fiber mixture, and mix for about 2 minutes. While the mixer is running, add 2.7 kilograms of vanilla flavor and 0.3 kilograms of caramel flavors (available as Givaudan Vanilla 10824-73 and Givaudan Caramel Toffee 11889-33), and mix for about 5 minutes to form the final mixture. Unload the vessel containing the final mixture into 1-2 transfer totes (vessels used to transfer material from the mixing vessel to the pre-kneader) at room temperature. Add the final mixture, adjusted to a temperature of from about 100° F. (about 38° C.) to about 120° F. (about 49° C.) to a pre-kneader, then to a final rope extruder and extrude into ropes, cool the ropes via a cooling tunnel (cooled to from about 40° F. (about 5° C.) to about 80° F. (about 27° C.)), and knife cut into individual pieces to form soft chews. Individual chews can be wrapped in poly-lined foil primary wrappers (available as Inner Wraps 32700X available from Flexible Packaging, Toronto, Ontario, Canada).

TABLE 1

Various Embodiments as can be made by methods such as the methods described in Examples 1-5.

| Ingredient | Example 1 (fiber/humectant) | | | Example 2 (fiber/humectant) | | | Example 3 (fiber/dual humectants) | | |
|---|---|---|---|---|---|---|---|---|---|
| | Amount in grams | w/w % | g/chew | Amount in grams | w/w % | g/chew | Amount in g | w/w % | g/chew |
| Inulin | 50 | 50 | 2.3 | 50 | 50 | 2.3 | 6,000 | 58.82 | 2 |
| Glycerin | | | | 10 | 10 | 0.5 | 1,200 | 11.76 | 0.4 |
| High Fructose Corn Syrup | | | | | | | 2,400 | 23.53 | 0.8 |
| 70% Sorbitol Solution | 10 | 10 | 0.5 | | | | | | |
| Crystalline Sorbitol | | | | | | | 280 | 2.75 | 0.1 |
| Flavor/Sweetener/ Preservative/Colorant mix | 1.11 | 1.11 | <0.1 | 1.11 | 1.11 | <0.1 | 200 | 1.96 | 0.1 |
| Water | 38.89 | 38.89 | 1.8 | 38.89 | 38.89 | 1.8 | 120 | 1.18 | <0.1 |

TABLE 1-continued

Various Embodiments as can be made by methods such as the methods described in Examples 1-5.

| | Example 4 (fiber/surfactant) | | | Example 5 (fiber/humectant/probiotic) | | g/tablet |
|---|---|---|---|---|---|---|
| Ingredient | Amount in kg | w/w % | g/chew | Amount in grams | w/w % | tablet wt 1 gram |
| Inulin | 60 | 61.23 | 2.82 | 140 | 68.97% | 0.69 |
| Sorbitol | | | | 10 | 4.93% | 0.05 |
| Lecithin | 3 | 3.06 | 0.14 | | | |
| Probiotic | | | | 20 | 9.85% | 0.10 |
| Microcrystalline Cellulose | | | | 30 | 14.77% | 0.15 |
| Flavor/Sweetener/Preservative/Colorant | 5 | 5.10 | 0.23 | 3 | 1.48% | 0.01 |
| Water | 30 | 30.61 | 1.41 | | | |

TABLE 2

Various Embodiments as can be made by methods such as the methods described in Examples 6-9.

| | Example 6 | | Example 7 | |
|---|---|---|---|---|
| Material | g/chew | Final w/w % | g/chew | Final w/w % |
| Artificial Caramel Flavor | <0.01 | 0.06 | | |
| Acesulfame Potassium | <0.01 | <0.01 | <0.01 | <0.01 |
| Chocolate Flavor #2 | <0.01 | 0.19 | | |
| Cocoa Powder | 0.38 | 8.25 | | |
| Corn Syrup Solids from Corn Syrup 43 DE source(50% solids) | 0.37 | 8.02 | 0.53 | 11.48 |
| Desugared Inulin | 2.26 | 49.23 | 2.11 | 45.88 |
| Glycerin 99% | 0.27 | 5.78 | 0.18 | 4.00 |
| Lecithin | 0.04 | 0.57 | 0.04 | 0.85 |
| Sucrose Solids from Liquid Sucrose Source (67% solids) | 0.33 | 7.17 | 0.57 | 12.38 |
| Milk Solids | 0.16 | 3.54 | 0.27 | 5.96 |
| Partially Hydrogenated Coconut Oil | 0.52 | 11.24 | 0.34 | 7.47 |
| Sodium Chloride | 0.02 | 0.51 | | |
| Sucralose | <0.01 | 0.02 | <0.01 | 0.01 |
| Sucrose (6X) | | | 0.13 | 2.84 |
| Vanilla Cream Flavor | <0.01 | 0.03 | | |
| Vanilla Flavor | | | 0.03 | 0.71 |
| Water (residual from cooking Liquid Sucrose and Corn Syrup) | 0.25 | 5.39 | 0.39 | 8.42 |

| | Examples 8 and 9 | |
|---|---|---|
| Material | g/chew | Final w/w % |
| Acesulfame Potassium | <0.01 | <0.01 |
| Caramel Toffee Flavor | <0.01 | 0.05 |
| Cocoa Powder | | |
| Corn Syrup Solids from Corn Syrup 43 DE source(50% solids) | 0.52 | 11.25 |
| Desugared Inulin | 2.07 | 44.99 |
| Glycerine 99% | 0.20 | 4.41 |
| Lecithin | 0.05 | 1.08 |
| Sucrose Solids from Liquid Sucrose Source (67% solids) | 0.56 | 12.14 |
| Milk Solids | 0.35 | 7.54 |
| Partially Hydrogenated Coconut Oil | 0.43 | 9.45 |
| Sodium Chloride | 0.02 | 0.39 |
| Sucralose | <0.01 | 0.01 |
| Vanilla Flavor | 0.02 | 0.43 |
| Water (residual from cooking Liquid Sucrose and Corn Syrup) | 0.38 | 8.26 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An extruded, ingestible composition, in the form of a chew, comprising:
   a. from about 40% to about 75% inulin, by weight of said composition;
   b. from about 0.001% to about 5% of a humectant component, by weight of said composition, wherein the humectants component is selected from the group consisting of glycerin, sorbitol, invert sugar, polyhydric alcohols, polyethylene glycol, propylene glycol, polyglycerol, gelatin, xanthan gums, carageenans, alginates, cyclomethicone, sodium hyaluronate, sodium lactate, triacetin, triethanolamine, and mixtures thereof; and
   c. from about 8% to about 40% of a carbohydrate component, by weight of the composition, selected from the group consisting of corn syrup, sucrose, liquid sucrose, polydextrose, trehalose, fructose, lactose, maltose, honey, glucose, galactose, and mixtures thereof;
   d. greater than 0% and less than 10% of a fat component, by weight of the composition; and
   e. from about 0.01% to about 3% of a surfactant component, by weight of the composition.

2. The composition of claim 1 wherein said inulin is desugared inulin.

3. The composition of claim 1 comprising about 50% to about 75% of said inulin, by weight of said composition.

4. The composition of claim 1 wherein the humectant component comprises glycerin.

5. The composition of claim 4 wherein said humectant component comprises a mixture of glycerin and sorbitol in a weight ratio of from about 2:1 to about 12:1.

6. The composition of claim 1, wherein said surfactant component is selected from the group consisting of: polyglycerol esters, glycerophospholipids, mono- and di-glycerides, sucrose monoesters, sorbitan esters, polyethoxylated glycols, agar, albumin, casein, glycerol monostearate, gums, egg yolk, lecithin, and mixtures thereof.

7. The composition of claim 1 wherein the carbohydrate component comprises corn syrup.

8. The composition of claim 7 wherein said carbohydrate component further comprises sucrose.

9. The composition of claim 8 wherein said carbohydrate component comprises a mixture of sucrose and corn syrup in a weight ratio of from about 1:1.1 to about 7:1.

10. The composition of claim 1 wherein the fat component comprises coconut oil.

* * * * *